(12) United States Patent
Wortelboer et al.

(10) Patent No.: US 10,690,657 B2
(45) Date of Patent: Jun. 23, 2020

(54) EPITHELIAL TISSUE MODEL

(71) Applicant: Nederlandse Organisatie voor toegepast-natuurwetenschappelijk onderzoek TNO, The Hague (NL)

(72) Inventors: Helena Maria Wortelboer, The Hague (NL); Dimitri Grossouw, The Hague (NL)

(73) Assignee: NEDERLANDSE ORGANISATIE VOOR TOEGEPAST-NATUURWETENSCHAPPELIJK ONDERZOEK TNO, 'S-Gravenhage (NL)

( * ) Notice: Subject to any disclaimer, the term of this patent is extended or adjusted under 35 U.S.C. 154(b) by 85 days.

(21) Appl. No.: 14/439,207

(22) PCT Filed: Oct. 29, 2013

(86) PCT No.: PCT/NL2013/050761
§ 371 (c)(1),
(2) Date: Apr. 28, 2015

(87) PCT Pub. No.: WO2014/069995
PCT Pub. Date: May 8, 2014

(65) Prior Publication Data
US 2015/0276713 A1    Oct. 1, 2015

(30) Foreign Application Priority Data

Oct. 29, 2012  (EP) ..................................... 12190442

(51) Int. Cl.
*C12Q 1/32*  (2006.01)
*G01N 33/50*  (2006.01)
(Continued)

(52) U.S. Cl.
CPC ........ *G01N 33/5035* (2013.01); *B01L 3/5021* (2013.01); *B01L 3/50255* (2013.01);
(Continued)

(58) Field of Classification Search
CPC ......... G01N 33/5035; G01N 2333/904; C12Q 1/32; C12M 25/04; C12M 23/02;
(Continued)

(56) References Cited

U.S. PATENT DOCUMENTS 4,264,204 A * 4/1981 McCormick .......... B01L 3/5082
                                                   356/246
4,669,763 A    6/1987 Phillips
(Continued)

FOREIGN PATENT DOCUMENTS

DE    103 09 348 A1    9/2004
EP    0 295 762 A2    12/1988
(Continued)

OTHER PUBLICATIONS

Hecht "English language translation of document DE 10309348", translated on Apr. 2, 2017.*
(Continued)

*Primary Examiner* — Liban M Hassan
(74) *Attorney, Agent, or Firm* — Knobbe, Martens, Olson & Bear, LLP

(57) ABSTRACT

A novel vial for holding a segment of epithelial tissue is provided. The vial is easy to assemble and allows horizontal alignment of the tissue sample. A device comprising the vial, to methods for generating the device, and to a multitude of said devices which allow medium throughput measurements of absorption, transport and/or secretion across an epithelial tissue are also provided.

13 Claims, 11 Drawing Sheets

(51) Int. Cl.
*C12M 1/12* (2006.01)
*B01L 3/00* (2006.01)
*C12M 3/00* (2006.01)

(52) U.S. Cl.
CPC ............ *C12M 21/08* (2013.01); *C12M 25/04* (2013.01); *C12Q 1/32* (2013.01); *B01L 2300/0609* (2013.01); *B01L 2300/0829* (2013.01); *G01N 2333/904* (2013.01)

(58) Field of Classification Search
CPC ...... C12M 23/58; C12M 29/10; C12M 41/48; C12M 35/08; C12M 41/44; C12M 27/00; C12M 23/04; C12M 23/34; C12M 23/38; C12M 23/44; C12M 21/08; B01L 3/5021; B01L 3/50255; B01L 2300/0829; B01L 2300/0609
USPC ........ 435/7.1, 7.92, 30, 287.1, 287.2, 288.7, 435/289.1
See application file for complete search history.

(56) References Cited

U.S. PATENT DOCUMENTS

| | | |
|---|---|---|
| 4,686,190 A | 8/1987 | Cramer |
| 4,737,262 A | 4/1988 | Franck et al. |
| 4,835,102 A * | 5/1989 | Bell .................. G01N 33/5014 424/572 |
| 4,897,193 A | 1/1990 | Cais et al. |
| 4,939,152 A * | 7/1990 | Barr ...................... C12M 23/08 215/320 |
| 5,022,411 A * | 6/1991 | Guirguis ............ A61B 10/0045 600/584 |
| 5,077,012 A * | 12/1991 | Guirguis ............ A61B 10/0045 422/401 |
| 5,358,690 A * | 10/1994 | Guirguis ............ A61B 10/0045 422/420 |
| 5,576,211 A * | 11/1996 | Falkenberg ............ C12M 23/24 435/297.1 |
| 5,662,230 A * | 9/1997 | Finneran ............... B65D 1/0246 215/252 |
| 6,251,681 B1 | 6/2001 | Davies |
| 2008/0076170 A1 | 3/2008 | Annala |
| 2009/0068674 A1* | 3/2009 | Dahm .................... B01J 19/249 435/6.12 |
| 2009/0196798 A1* | 8/2009 | Sassa .................... A61J 1/1406 422/400 |

FOREIGN PATENT DOCUMENTS

| | | | |
|---|---|---|---|
| EP | 2 548 943 A1 | 1/2013 | |
| GB | 2 082 091 A | 3/1982 | |
| WO | WO-2012079577 A1 * | 6/2012 | ............ C12M 23/24 |

OTHER PUBLICATIONS

Harvard Apparatus: "Diffusion Chamber System User's Manual", Mar. 16, 2012, pp. 1-28.
International Search Report and Written Opinion dated Feb. 3, 2014 for PCT/NL2013/050761.

* cited by examiner

EPITHELIAL TISSUE MODEL

CROSS REFERENCE TO RELATED APPLICATIONS

This application is the U.S. National Phase of International Application No. PCT/NL2013/050761, filed Oct. 29, 2013, designating the U.S. and published in English as WO 2014/069995 A1 on May 8, 2014 which claims the benefit of European Patent Application No. 12190442.9, filed Oct. 29, 2012. Any and all applications for which a foreign or domestic priority claim is identified in the Application Data Sheet as filed with the present application are hereby incorporated by reference under 37 CFR 1.57.

FIELD

The invention relates to an improvement of a device for measuring absorption, transport and/or physiological functions across an epithelial tissue. More specifically, it relates to an improvement which allows the horizontal mounting of epithelial tissues with varying thickness, allowing direct contact of a compound under investigation with the epithelial tissue. In addition, the improved device can be assembled into multiwell formats, allowing the simultaneous analyses of multiple measurements. Moreover, standardized multiwell formats allow the use of robotics for automation of various liquid handlings.

Description of the Related Art

To understand how epithelial tissue functions, as well as its pathophysiology, it is crucial to use models that mimic the natural tissue in view of diversity of cell types, structure, mechanical properties and biochemical microenvironment. Unfortunately, most studies on cell and tissue regulation have relied on the analysis of cells that were grown in two-dimensional (2D) cell-culture models. However, these models fail to reconstitute the in vivo cellular microenvironment and, as a result, they do not maintain their differentiated functions.

Efforts to address these limitations led to the development of 3D cell-culture models in which cells are grown embedded in an extracellular matrix. This approach enhances expression of differentiated functions and improves tissue organization (Pampaloni et al. (2007). Nat Rev Mol Cell Biol 8: 839-84). Nevertheless, also these 3D culture models fail to reconstitute features of living tissues that are crucial for their function.

In addition, current methods and means do not allow medium throughput permeation studies, such as analyses of absorption, transport and/or secretion, across an epithelial tissue. For example, known transwell plates are not suited for measuring absorption, transport and/or secretion across a sample of an epithelial tissue as the tissue sample will not sufficiently adhere to the membranes of the transwell plates so that leakage can not be avoided. In addition, the mounting of segments of epithelial tissues onto commercial systems, for example Ussing chambers (Rozehnal et al. (2012) Eur J Pharm Sci 46: 367-73), Franz cell systems (Flynn et at (1999) Pharm Res 16: 1325-30), NaviCyte chambers (Palamakula et al. (2005) Pharmazie 60: 212-4) and EasyMount Verticle chambers, is difficult. The vertical alignment of the tissue sample in an Ussing chamber, NaviCyte chamber or EasyMount Verticle chamber system imposes experimental conditions that are substantially different from the in vivo situation in case interactions are studied with test substances which are not completely dissolved in an aqueous solution, for example digested food compounds, microbiota, cream. Moreover, these systems do not allow the simultaneous preparation and analyses of multiple segments of epithelial tissues at the same time, thereby having a low throughput (ranging from 6-12 segments per system per day).

SUMMARY

Hence, there is a clear need for the development of methods and means that allow permeation studies, such as analyses of absorption, transport and/or secretion, across an epithelial tissue at medium throughput (ranging from 24-48-72 segments per system per day).

The present invention is directed to a novel device that allows horizontal mounting of a segment of epithelial tissue. The horizontal mounting enables the direct contact of test compounds with the epithelial tissue. Moreover, segments of epithelial tissue with varying thickness can easily be mounted in the device. Multiple devices can easily be arrayed allowing medium throughput analyses of absorption, transport and/or secretion across the epithelial tissue. In addition, the device according to the invention is generated from disposable material, which will reduce a risk of contamination of the mounted device.

Detailed Description of Certain Embodiments of the Invention

The invention therefore provides a vial or vial assembly for holding a segment of epithelial tissue, the vial having a neck and a first open end at the top of the neck, whereby a rim surrounds the open end, the rim having an upper surface facing the open end, whereby the neck and the rim of the first open end of the vial are suited for capping with a crimp cap, the vial characterized by having a second open end distal to the neck.

A preferred vial or vial assembly for holding a segment of epithelial tissue according to the invention has a neck and a first end at a top of the neck, wherein at the first end a rim is provided that defines a first opening, wherein an upper surface of the rim faces away from the neck, wherein the neck and the rim define a cap receiving area for receiving a crimp cap, characterized in that the vial has a second open end located distal to the neck and wherein a ring of inert material is provided adjacent the upper surface of the rim, of which an inner diameter is substantially equal to a diameter of the first opening.

It was found that especially stiff and thick epithelial tissue can easily be mounted on a device of the invention, in contrast to systems that are available in the art. Surprisingly, the mounted tissue did not show any signs of disturbance, toxicity, and/or stress, in contrast to tissue that is mounted on other devices.

Crimp cap vials having a closed end distal to the open crimp capped end are known in the art. For example, 2 ml (12×32 mm) crimp top vials are available from Agilent Technologies (Santa Clara, Calif.). Crimp top vials ranging between 0.1 ml and 1.2 ml are available from Fisher Scientific (Pittsburgh, Pa.). Preferred crimp top vials are headspace vials, for example 20 ml headspace vials from Alltech Associates, Inc (Deerfield, Ill.).

Possible internal diameters of the crimp cap vials at the open crimp capped end range from 4.05 mm (0.75 ml crimp top vial) to 12.75 mm (20 ml crimp top vial). Corresponding exposure surface areas could range from 0.52 $cm^2$ (0.75 ml crimp top vial) to 3.17 cm² (20 ml crimp top vial), based on the opening in the crimp caps.

A vial according to the invention can for instance be prepared by removing the closed end distal from a known crimp cap vial, for example with a glass cutter. The resulting internal diameters of the opened distal end range from 6.55 mm (0.75 ml crimp top vial) to 20.65 mm (20 ml crimp top vial).

A vial according to the invention may be composed of any material known in the art, including glass, polypropylene, low-density polyethylene, high-density polyethylene, polymethyl-pentene and polystyrene. A preferred vial according to the invention is composed of glass such as, for example, borosilicate clear glass Type 1, Class A or 51A amber glass.

Said crimp cap is, for example, a POLY CRIMP™ Seal crimp cap, which is available from F.J. Finneran (Vineland, N.J.) or, preferably, a standard crimp cap, such as a standard aluminum crimp cap, for example aluminium knurled caps from Perkin Elmer 15 (the Netherlands). Methods for providing a crimp cap onto a crimp cap vial are known in the art, including vial crimping hand tools and automated vial crimpers. Suitable crimping tools are available, for example, from Kebby Industries, Inc (Rockford, Ill.) and from Alltech Associates, Inc (Deerfield, Ill.) such as a hand crimper and a hand decapper.

The invention further provides a vial according to the invention comprising a segment of epithelial tissue, the segment being positioned on the upper surface of the rim, with the apical side of the epithelial tissue facing the first open end, whereby a ring of inert material is positioned on one side, preferably the apical side, of the epithelial tissue, and whereby a crimp cap provides a tight seal of the first end of the vial.

A preferred vial according to the invention is characterized by having a second open end distal to the neck; further comprising a receiving area for receiving a segment of epithelial tissue, wherein the receiving area is provided adjacent the ring of inert material, at a side of the ring facing away from the rim, such that when a segment of epithelial tissue is received in the receiving area, an apical side of the epithelial tissue faces the first opening and a basolateral side of the epithelial tissue faces away from the first opening, whereby a ring of inert material is positioned on the apical side of the epithelial tissue, and wherein the crimp cap is provided on the cap receiving area to provide a tight seal to the first end of the vial.

Epithelial tissue is specialized tissue that forms the lining of all internal and external body surfaces. Epithelial tissue is made up of cells closely packed and ranged in one or more layers. Epithelial tissue that occurs on surfaces on the interior of the body is known as endothelium. Epithelial tissue, regardless of the type, is usually separated from the underlying tissue by a thin sheet of connective tissue, which is termed the basement membrane. The basement membrane provides structural support for the epithelium and also binds it to neighboring structures.

There are two types of epithelial tissue depending on the number of layers of which it is composed. Epithelial tissue which is only one cell thick is known as simple epithelium. If it is two or more cells thick such as the skin, it is known as stratified epithelium.

Simple epithelium can be subdivided according to the shape and function of its cells. Squamous (pavement) epithelium lines areas where passive diffusion of gases occur, for example capillaries, the pericardial, pleural, and peritoneal cavities, as well as the alveoli of the lungs. Simple cuboidal epithelium is found in glands and in the lining of the kidney tubules as well as in the ducts of the glands. This epithelium also constitutes the germinal epithelium which produces the egg cells in the female ovary and the sperm cells in the male testes. Glandular epithelium with goblet cells is often present in specialised gland cells which are capable of synthesising and secreting certain substances such as enzymes, hormones, milk, mucus, sweat, wax and saliva. A portion of the epithelial tissue often becomes invaginated, thereby forming a multicellular gland. An example of a multicellular gland is the salivary gland.

Stratified epithelium is composed of several layers of cells. The top cells are often flat and scaly and it may or may not be keratinized (i.e. containing a tough, resistant protein called keratin). The mammalian skin comprises dry, keratinized, stratified epithelium. Further examples of keratinized stratified epithelium are provided by the dorsum of tongue and the hard palate. The lining of the mouth cavity is an example of an un-keratinized, stratified epithelium.

A preferred epithelial tissue is provided by the stratified squamous, non-keratinized epithelium of the oesophagus, the simple columnar epithelium of the stomach, small intestine, large intestine and rectum, and the stratified squamous epithelium of the anus, vagina, and skin.

Said epithelial tissue is preferably an epithelial tissue from a vertebrate, preferably a mammal, more preferably from a rodent such as a mouse or a rat, more preferably from a mammal of the Suidae family including a wild and domestic pig, more preferably from a primate, most preferably from a human.

A most preferred epithelial tissue is provided by the epithelium of the small intestine, large intestine and skin from a pig or human. In the development of pharmaceuticals and nutritional products, oral bioavailability is an important issue as this process can hamper the efficacy of the active compound. To reveal predictive information on the fraction absorbed in humans, currently in silico tools, in vitro studies (mainly cell lines) and animal studies are performed prior to the human studies. The desired degree of accuracy and predictive power of the assay is dependent on the stage in product development.

After oral dosing, the compound has to cross the intestinal barrier before it will enter the blood stream. A compound's kinetics over a epithelial barrier may be depending on mucosal interaction, passive diffusion, carrier-mediated or active transport and/or metabolism. Transporters and metabolizing enzymes can play a role in the uptake and efflux of compounds thereby affecting the kinetic behaviour in the body.

A further preferred epithelial tissue is an epithelial tissue from a diseased vertebrate, such as intestinal tissue from a person suffering from an inflammatory bowel disease such as Crohn's disease and ulcerative colitis, collagenous colitis, lymphocytic colitis, ischaemic colitis, diversion colitis, Behçet's disease, indeterminate colitis, or intestinal interstitial cystitis, and skin tissue from a person suffering from psoriasis, lupus, or scleroderma. This will allow to determine effects of diseased tissue on, for example, absorption, transport and/or secretion across an epithelial tissue.

Yet a further preferred epithelial tissue is an epithelial tissue from a transgenic animal, for example a knock-in mouse or a knock-out or knock-down mouse, in which the effect of the additional expression of a gene, or the effect of the downmodulation or elimination of the expression of a gene, on the epithelial tissue can be determined.

It is preferred that the basolateral side of the epithelial tissue is covered by a support, when the epithelial tissue is mounted into a vial of the invention. Said support is preferably a mesh of an inert material, preferably a nylon or polypropylene mesh. A preferred mesh is a woven mesh, for example NITEX 06-390/47 (woven mesh; opening 390 μm; 47% open area; thickness 310 μm) from Sefar B.V. (Lochem, the Netherlands).

Said support is preferably provided between the receiving area and the crimp cap, such that when a segment of epithelial tissue is received in the receiving area, the basolateral side of the epithelial tissue is covered by said support.

It is preferred that the epithelial tissue is covered by a ring of an inert material, preferably a Teflon or silicon ring, or a combined silicon/Teflon ring, for example a septum such as an O-ring of Interscience B.V. (Breda, the Netherlands). Said ring will assist in obtaining a tight seal by the crimp cap at the first end of the vial. The size of the ring is preferably such that the ring covers substantially only the upper surface of the rim. It is further preferred that only a small portion of the apical side of the epithelial tissue is covered by the ring. It is further preferred that a substantial part of the first opening provided at the first end of the vial, more preferably the complete the first opening (indicated as d in FIG. 2), is covered only by the epithelial tissue.

In an alternative embodiment, a support is present on the apical side and a ring of inert material on the basolateral side of the epithelial tissue facing away from the first opening.

In a preferred embodiment, the outer diameter of the first opening is about 2× the inner diameter of the first opening, whereby a ring covers the upper surface of the rim. In this embodiment, about 33% of the surface of an epithelial tissue that is mounted on the vial is not in contact with the ring. It is further preferred that the inner diameter of the opening of the first end of the vial is substantially identical to the inner diameter of the opening of the ring of inert material and identical to the inner diameter of the opening of the crimp cap.

The invention further provides a device comprising a vial according to the invention and a container for holding the vial, the container having a closed bottom and side walls, whereby the container is open on one end, whereby the vial is mounted into the container with the first open end of the vial facing the closed bottom of the container, and whereby the crimp cap is not in contact with the closed bottom of the container.

Said device for measuring absorption, transport and/or secretion across an epithelial tissue, preferably comprises at least one vial according to the invention and a container for holding the at least one vial, wherein the container comprises a closed bottom and an open top side facing away from the bottom, wherein the vial is received in the container with the first end of the vial facing the bottom of the container, such that the crimp cap is located at a distance from the bottom such that the crimp cap does not abut the bottom of the container.

Said device preferably comprises at least one mounting element provided adjacent the at least one open end of the container configured to engage the vial at the second end thereof. It is preferred that said mounting element does not provide an air-tight engagement of the vial to the container, preferably by having an opening allowing air exchange between the container and the outer environment.

The dimensions of said container are such that the vial can be easily positioned into the container. However, the dimensions of the container are preferably only slightly increased compared to the dimensions of the vial so as to limit the amount of medium that is to be deposited in the container. For example, when a vial of 12 mm width and 32 mm height (outside sizes) is used, the width of the container is preferably between 13 and 25 mm, more preferred between 14 and 20 mm, more preferred about 15 mm, whereby the height is the container is preferably less than the height of the vial, such as, for example 20 mm. A preferred container for a 20 ml vial is a 25 ml beaker from Fisher Scientific (Landsmeer, the Netherlands).

It is preferred that the vial and the container form a matched assembly as a part of the device according to the invention. The vial in a matched assembly preferably has a marker, for example a notch or a thickening, at a vertical position at the side of the vial which indicates that the vial is mounted into the container with the first end of the vial facing the closed bottom of the container while the crimp cap is not in contact with the closed bottom of the container. A preferred marker is provided by a thickening on the side of the vial which ensures that the vial can not be positioned into the container such that the crimp cap is in contact with the closed bottom of the container.

Said container may be composed of any material known in the art, including glass, polypropylene, low-density polyethylene, high-density polyethylene, polymethyl-pentene and polystyrene. A preferred container is composed of glass such as, for example, borosilicate clear glass Type 1, Class A or 51A amber glass.

The invention further provides a device comprising a multitude of containers holding a multitude of vials, respectively, according to the invention. Said multitude is preferably arranged in an arrayed format, such as for example, in a line or in a square. It is further preferred that the distances between the containers is constant in the arrayed format.

A preferred device comprises an arrayed format such as 6, 12, 24, 48 or 96 containers, which are preferably in a (2*3), (4*3), (6*4), (6*8) and (12*8) format, respectively. The outer dimensions of the devices are such that the device can easily be handled. It is preferred that the device with the multitude of containers preferably in an arrayed format of 6, 12, 24, 48 or 96 containers, has a footprint (length×width) of 127.76×85.48 mm, which allows the use of, for example, multichannel pipettes and/or robotics for liquid handling.

A preferred method for generating a vial comprising epithelial tissue according to the invention comprises preparing a segment of an epithelial tissue, mounting the basolateral side of the epithelial segment on a support, mounting the supported segment on a vial according to the invention, whereby the apical side of the epithelial tissue faces the first open end of the vial, mounting a ring of inert material onto the apical side of the epithelial tissue, and providing a crimp cap to the first open end to obtain a tight seal of the first end of the vial. It is preferred that the epithelial tissue is cooled, for example on ice, during the generation of the vial.

A preferred method for generating a vial with a segment of epithelial tissue according to the invention comprises the steps of providing a vial according to the invention, preparing a segment of an epithelial tissue, mounting a basolateral side of the epithelial segment on the support, mounting a ring of inert material onto the apical side of the epithelial tissue, mounting the supported segment on an upper surface of the rim, such that the ring of inert material abuts the upper surface and the apical side of the epithelial tissue faces the first opening of the vial, and providing a crimp cap on the cap receiving area to obtain a tight seal on the first end of the vial.

A segment of an epithelial tissue is preferably prepared by isolating a piece of epithelial tissue, for example intestinal tissue. The outer muscular layers are preferably removed.

Segments of the resulting mucosa and submucosa layers can be prepared by methods known in the art, for example by punching with a hollow punch, for example a ⅛-inch to 2-inch hollow punch from Mayhew (Turner Falls, Mass. 01376). Segments of other epithelial tissue, such as skin tissue, are preferably prepared by similar methods. It is preferred that most, or substantially all, of the hypodermal layer is removed before mounting of a segment into a vial.

A preferred method for generating a device comprising a multitude of vials comprising epithelial tissue according to the invention comprises (a) performing the method for generating a vial comprising epithelial tissue to prepare a first vial, (b) cooling at least the first end comprising the segment of an epithelial tissue, and repeating steps (a) and (b) until the multitude of vials is prepared.

Said method for generating a multitude of vials with a segment of epithelial tissue, preferably comprises (a) performing the method of the invention to prepare a first vial, (b) cooling at least the first end comprising the segment of an epithelial tissue, repeating steps (a) and (b) until the multitude of vials is prepared.

In a more preferred method for generating a device comprising a multitude of vials comprising epithelial tissue according to the invention, multiple segments of an epithelial tissue are prepared and collected in a receptacle comprising a physiological fluid, followed by mounting the prepared segments on a support and mounting the supported segments on vials according to the invention. It is preferred that the epithelial tissue is cooled, for example on ice, during the generation of the vials.

The invention further provides a method for measuring absorption, transport and/or secretion across an epithelial tissue, the method comprising providing the device comprising an epithelial tissue according to the invention, providing a physiologically relevant buffered medium in the vial onto the apical site of the segment of epithelial tissue, providing a physiologically relevant buffered medium to the container, whereby the height of the buffered medium in the vial is substantially equal to the height of the buffered medium in the container, applying a substance to the medium at the apical site of the segment of epithelial tissue, and measuring the amount of substance that appears in the medium of the container, and/or and measuring the amount of substance that accumulates in the epithelial tissue, during and/or at the end of the incubation.

Said method for measuring absorption, transport and/or secretion across an epithelial tissue, preferably comprises providing a device according to the invention, wherein an epithelial tissue is provided in the at least one vial of the device, providing a buffered medium in the vial onto the apical site of the segment of epithelial tissue, providing a buffered medium to the container, wherein a height of the buffered medium in the vial is substantially equal to a height of the buffered medium in the container, applying a substance to the medium at the apical site of the segment of epithelial tissue, and measuring the amount of substance that appears in the medium of the container, and/or measuring the amount of substance that accumulates in the epithelial tissue, during the incubation and/or at the end of the incubation.

A physiologically relevant buffered medium is preferably Krebs-Ringer Bicarbonate (KRB) buffer (10 mM D-Glucose; 0.5 mM MgCl2; 4.6 mM KCl; 120 mM NaCl; 0.7 mM $Na_2HPO_4$; 1.5 mM $NaH_2PO_4$), with 25 mM 4-(2-hydroxyethyl)-1-piperazineethanesulfonic acid (HEPES) and 15 mM $NaHCO_3$, pH adjusted to 7.4 with NaOH. The incubation buffer can further be enriched for example with essential amino acids, hormones and/or growth factors.

The substance is preferably labeled prior to applying the substance to the medium at the apical site of the segment of epithelial tissue. A preferred label is a fluorescence label or a radioactive label such as, for example, $^3H$ or $^{14}C$.

A substance can be measured by analytical techniques, for example using Absorbance, Fluorescence, High Pressure Liquid Chromatography (HPLC), Liquid chromatography-Mass Spectrometry (LCMS), Liquid chromatography-Tandem Mass Spectrometry (LC-MSMS), Enzyme-linked immunosorbent assay (ELISA), Radio-Immuno assay (RIA).

A test compound can further be added that either enhances or inhibits secretion in order to identify general or specific cellular mechanisms, neuronal circuits, neurotransmitters and -receptors and/or ion channels.

A preferred method for measuring absorption, transport and/or secretion across an epithelial tissue of the invention further comprises adding a marker to the apical site of the segment of epithelial tissue, and measuring the amount of marker that appears in the medium of the container. Said marker, for example fluorescein isothiocyanate-dextran (FD4; Sigma-Aldrich Chemie B.V., Zwijndrecht, the Netherlands) is used as a control for indicating, for example, leakage of the seal of the first end of the vial comprising the epithelial tissue. A leakage of FD4 below 0.2% of the apical dose in the medium of the container indicates no leakage of the seal.

Said methods for measuring absorption, transport and/or secretion across an epithelial tissue are preferably performed in an incubator. It is further preferred that the device and/or the containers are moved during the measurements, preferably on a shaking or rocker platform. The incubator preferably provides high oxygen conditions, such as more than 50% O2, more preferred about 70% O2. The incubator preferably also provides a humidified atmosphere to prevent evaporation from the vials and/or the containers. The incubator preferably also provides for carbon dioxide in the atmosphere, such as for example 5% CO2, which helps to maintain the pH of the buffered medium at the preset value. It is preferred that the device is allowed to acclimatize in the incubator for a limited period of time, for example 10 minutes, 20 minutes, 30 minutes, 40 minutes, 50 minutes or 60 or more minute, preferentially 30 minutes, prior to the start of the measurements.

When required, electrodes can be provided to the vials and container to make electrophysiological measurements such as, for example, net ion transport across an epithelium and/or the barrier function between the apical and basolateral sides. A preferred electrode is an Ag/AgCl reference electrode which is contained in a glass barrel that terminates in a micro-porous ceramic tip. The barrel is filled with a suitable electrolyte solution, preferably the buffer used for the external media or 3M KCl, and is preferably refillable. Said electrodes may be positioned, for example, in the elongate, cylindrical body 110 of the vial, in the container, and/or in the mesh material that covers the epithelial tissue.

The invention further provides a use of a crimp cap for mounting a segment of epithelial tissue on a vial. The invention further provides a use of a, vial for holding a segment of epithelial tissue, the vial having a neck and a first end at a top of the neck, wherein a rim is provided at the first end that defines a first opening, wherein an upper surface of the rim faces away from the neck, wherein the neck and the rim define a cap receiving area for receiving a crimp cap, characterized in that the vial has a second open end located distal to the neck and wherein a ring of inert material is provided adjacent the upper surface of the rim, of which an inner diameter is substantially equal to a diameter of the first opening, for holding a segment of epithelial tissue.

The present methods, vials and devices are designed for transepithelial permeation studies from the apical side (for example the outside of skin, or the lumen side of intestinal tissue) to the basolateral side (for example the side facing the hypodermis of skin, or the blood side of intestinal tissue). It will be clear to a person skilled in the art that methods, vials and devices for transepithelial permeation studies from the basolateral side to the apical side are also possible using the methods, vials and devices according to the invention. This can be achieved, for example, by providing a vial according to the invention comprising a segment of epithelial tissue, the segment being positioned on the upper surface of the rim, with the basolateral side of the epithelial tissue facing the first open end, whereby a ring of inert material is positioned on the apical side of the epithelial tissue, and whereby a crimp cap provides a tight seal of the first end of the vial. A substance, for example a labeled substance, can be applied to the medium at the basolateral site of the segment of epithelial tissue in the container, followed by measuring the amount of label that appears at the apical side in the medium of the vials.

The aforementioned and other features and advantages of the invention will be more fully understood from the following detailed description of certain embodiments of the invention, taken together with the accompanying drawings, which are meant to illustrate and not to limit the invention.

BRIEF DESCRIPTION OF THE DRAWINGS

It is noted that identical or corresponding elements in the different drawings are indicated with identical or corresponding reference numerals.

DETAILED DESCRIPTION

Figure 2:
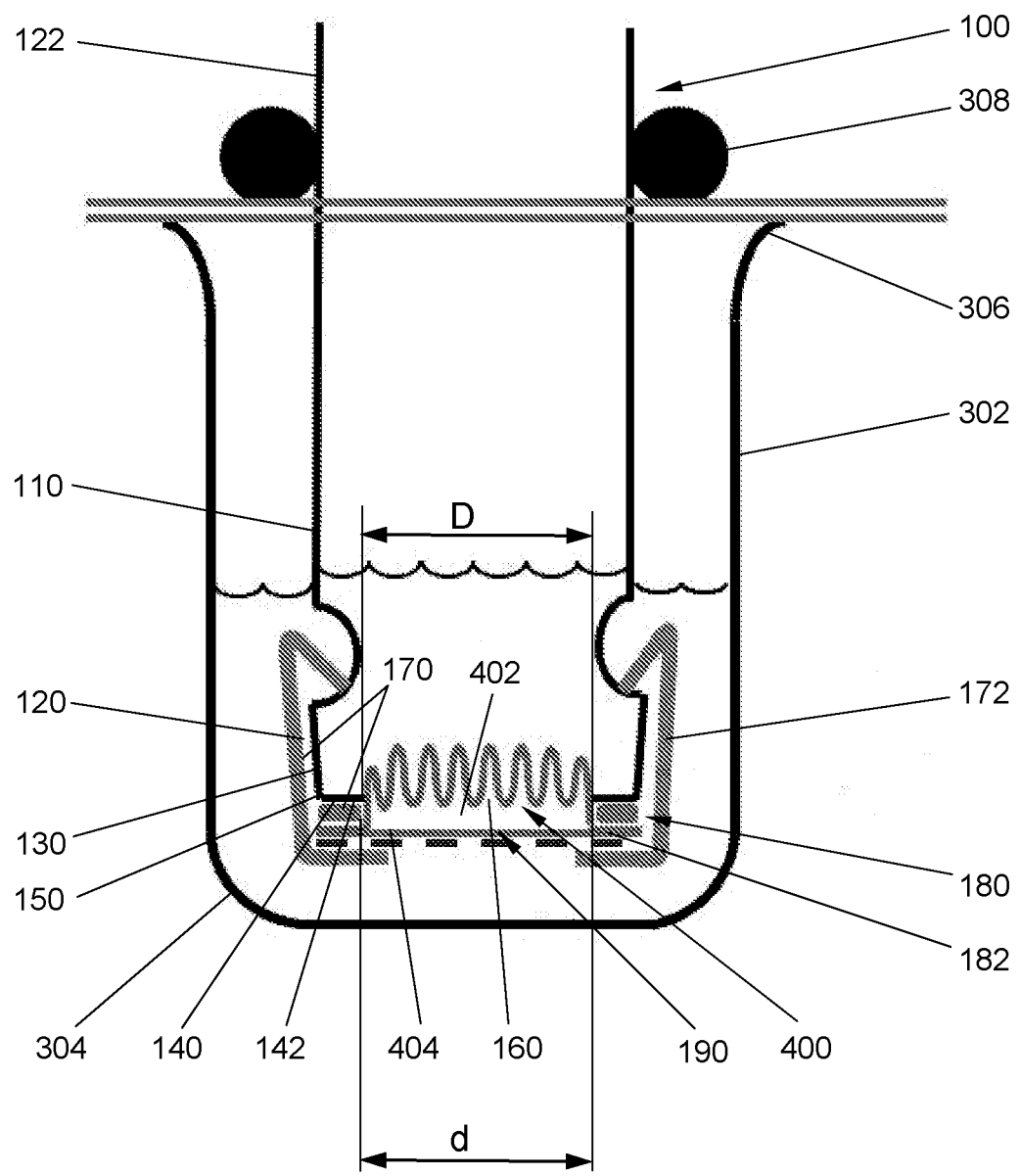
FIG. 2. Schematic view of a prototype of the epithelial tissue system mounted together.
Figure 3:
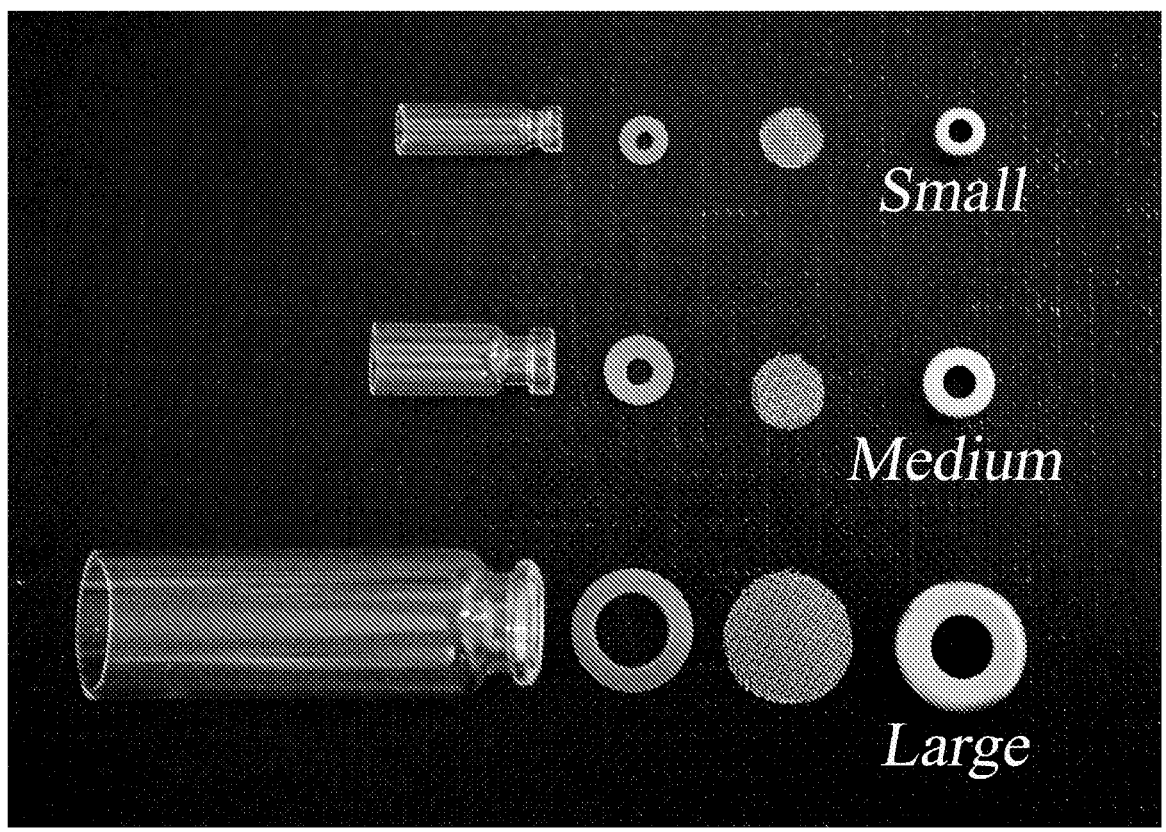
FIG. 3. Photograph of an example of different sizes which can be used in the Epithelial Tissue Model.
Figure 4:
FIG. 4. Photograph of a prototype of the epithelial tissue system mounted together. Please note the possibility to shake the tissue on, for example, a rocker platform.

FIG. 2 schematically illustrates an exemplary embodiment of a vial 100 according to the present invention. The vial 100 is configured for holding a segment of epithelial tissue 400 such that it can be used in a device 300 for measuring absorption, transport and/or secretion across said tissue. Such device 300 will be described with FIG. 5. The vial 100 comprises a substantially elongate, cylindrical body 110. Adjacent a first end 120 of the vial, a neck 130 is provided. At a top of the neck 130, thus at the first end 120 of the vial, a rim 140 is provided. The rim 140 extends from a perimeter 150 of the first end 120 inward thereby defining a first opening 160. An upper surface 142 of the rim 140 faces away from the neck 130. The neck 130 and the rim 140, at least the upper surface 142 thereof, define a cap receiving area 170 for receiving a crimp cap 172. At a second side of the vial 100 facing away from the first end 120, a second open end 122 is provided. The second open end 122 is located distal to the neck 130.

At the upper surface 142 of the rim 140, a ring 180 of inert material is provided in abutment with the rim 140. The ring 180 may for instance be of Teflon. The inner diameter d of the ring 180 is substantially equal to the diameter D of the opening 160 defined by the rim 140. At a side of the ring 180 of inert material that faces away from the rim 140, a receiving area 190 for receiving the segment 400 of epithelial tissue is provided. In the vial 100 according to FIG. 2, such segment 400 is received in the receiving area 190. The apical side 402 of the epithelial tissue 400, when received in the receiving area 190, faces the first opening 160 and the basolateral side 404 of the epithelial tissue faces away from the first opening 160. The basolateral side 404 is provided in abutment with a support 182. The support 182 may be of a mesh, for instance a nylon or polypropylene mesh. A crimp cap 172 is crimped on the cap receiving area 170. The cap 172 extends partly along an outer surface of the support 182, thus the side of the support facing away from the tissue 400, and along an outer circumferential wall part that forms the neck 130.

To generate the above described vial 100 comprising a segment 400 of epithelial tissue, first a segment 400 of said epithelial tissue is prepared. Then, the basolateral side 404 of the segment 400 is mounted to the support 182. Then, the ring 180 of inert material is mounted on the apical side 402 of the segment of epithelial tissue 400. The segment 400 is then mounted on the upper surface 142 of the rim 140 such that the ring 180 of inert material abuts the upper surface 142 of the rim 140 and the apical side of the epithelial tissue faces the first opening 160 of the vial 100. Subsequently, the crimp cap 172 is crimped on the cap receiving are 170 to obtain a tight seal on the first end 120 of the vial 100.

In a different embodiment of the vial 100 (not shown), the different elements provided at the first end 120 of the vial 100 may be arranged in a different order than in the embodiment as described with and shown in FIG. 2. In such embodiment, the support 182 is provided adjacent the upper surface 142 of the rim 140 such that a first surface, at least along the perimeter of the support 182 abuts the upper surface 142 of the rim 140. On the opposite second surface of the support 182, thus the surface facing away from the rim 140, a sample of epithelial tissue 400 is provided such that the apical side 402 of the tissue 400 faces the support 182 and also the first opening 160. The basolateral side 404 faces away from the support 182 and from the rim 140. On the basolateral side 404 of the segment 400 of epithelial tissue, a ring 180 of inert material is provided, such that it covers the segment 400 of epithelial tissue along the outer perimeter thereof. A crimp cap is crimped on the cap receiving area 170. The cap 172, at least a surface thereof facing the rim 140 clamps the ring 180, the segment 400 of epithelial tissue and the support 182 against the upper surface 142 of the rim 140.

To generate the above described vial 100 according to the second (not shown) embodiment first a segment 400 of said epithelial tissue is prepared. Then, the apical side 402 of the segment 400 is mounted to the support 182. Then, the ring 180 of inert material is mounted on the basolateral side 404 of the segment of epithelial tissue 400. The segment 400 is then mounted on the upper surface 142 of the rim 140 such that the support 182 abuts the upper surface 142 of the rim 140 and the ring 180 of inert material faces away from the first opening 160 of the vial 100. Subsequently, the crimp cap 172 is crimped on the cap receiving are 170 to obtain a tight seal on the first end 120 of the vial 100.

Figure 5:
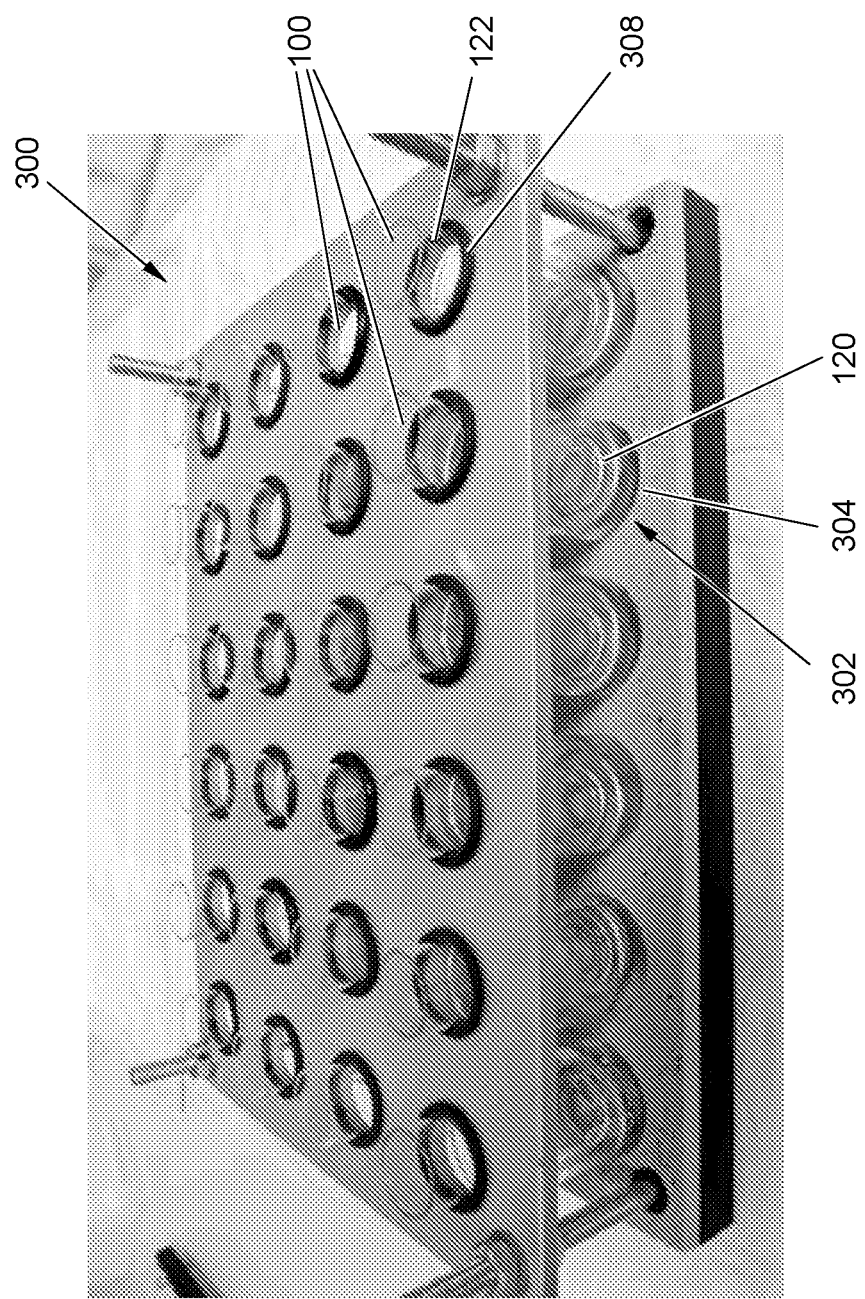
FIG. 5. The intestinal tissue model mounted together mounted in a 24 vial setting. The whole model can be placed on a rocker platform into an atmosphere controlled incubator.

In FIG. 5 an exemplary embodiment of a device 300 for measuring absorption, transport and/or secretion across an epithelial tissue is shown. The device 300 comprises a multitude of containers 302 (see also FIG. 2) holding a multitude of vials 100. Each container 302 comprises a closed bottom 304 and an open top side 306 facing away from the bottom 304. The vial 100 is inserted in the container 300 such that the crimp cap 172 is positioned opposite the bottom 304 at a short distance from said bottom 304. Adjacent the top side 306 (see also FIG. 2) of the container 302, a mounting element 308 is provided. The mounting element 308 is configured to engage, in the shown embodiment by means of a clamping ring, the vial 100 at the second open end 122. When in the mounted position, the vial 100 is positioned such that the crimp cap 172 does not abut the bottom 304. In the shown embodiment of the device 300, the device 300 comprises 24 containers for receiving vials 100. The device 300 may however instead comprise 6, 12 or 48 containers. Preferably, the footprint (length×width) of the device 300 may be approximately 127.76×85.48 mm.

EXAMPLES

Example 1

Transport of Test Compounds Across Intestinal Tissue In Vitro

The gastro-intestinal tract is the primary site for the intake, processing, and absorption of pharmaceuticals and nutritional products. With the herein presented Epithelial Tissue Model using intestinal wall segments derived from pigs, the complex integrated physiology occurring in intact intestinal tissue can be studied. The gastrointestinal tract of pigs closely resembles that of humans, and having a whole intestine available offers the opportunity to work with different parts of the intestine, such as the duodenum, jejunum, ileum, or colon.

Figure 1:
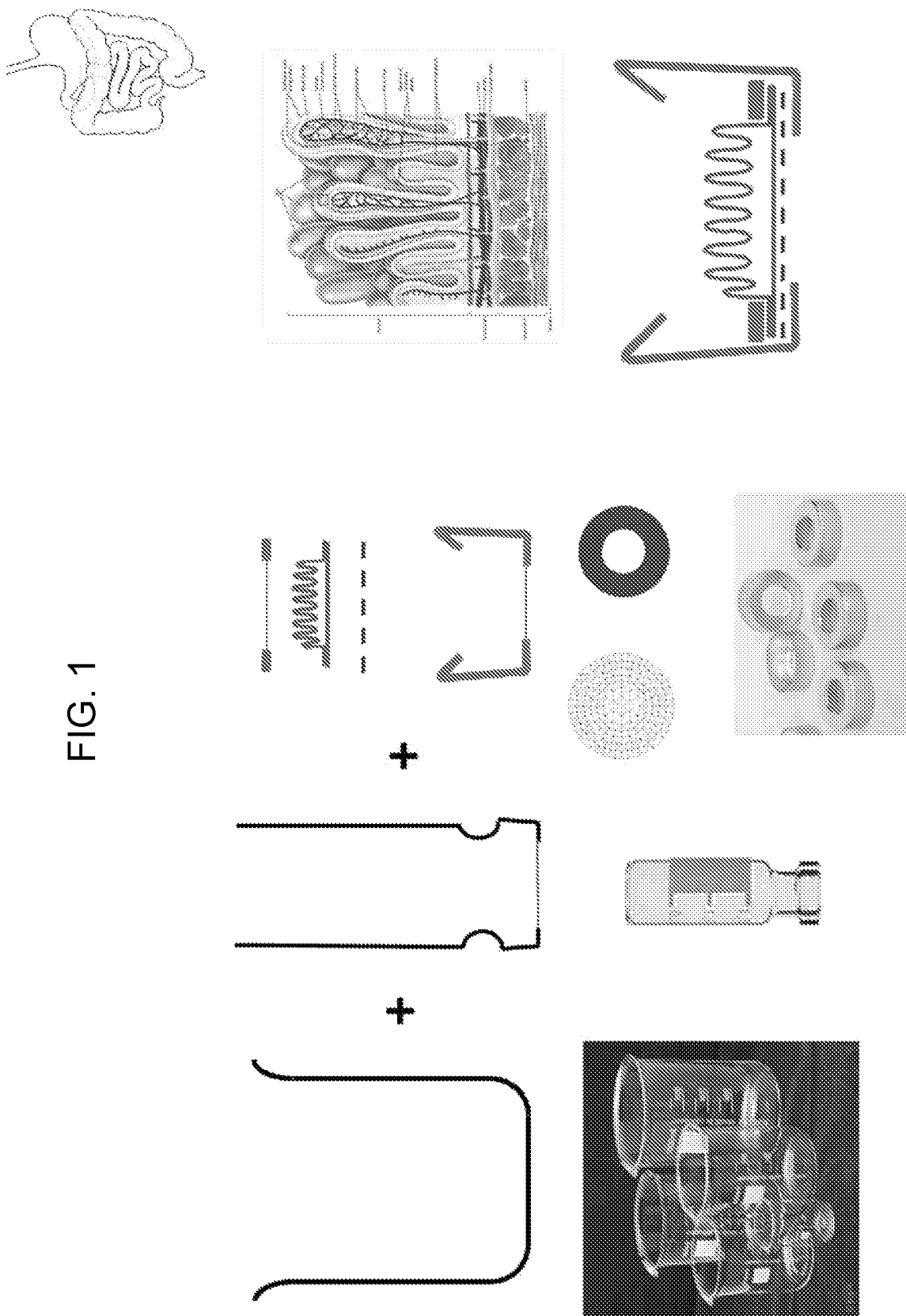
FIG. 1. Schematic view of the different parts of a prototype of the Intestinal Epithelial Model.

Method for Intestinal Tissue Incubation (See FIGS. 1-5)
1. After anesthesia of the animal and resection of intestinal tissue, the tissue was directly added to ice-cold carbonated (5% $CO_2$ and 95% $O_2$) KRB buffer, pH 7.4, further referred to as KRB buffer.
2. Intestinal tissue was transported to the test site in ice-cold KRB buffer
3. At the test site, the intestinal tissue was cut open, rinsed with ice-cold KRB buffer when needed, placed on a petridish, submerged in ice-cold KRB buffer and muscle layers were stripped of.
4. Intestinal segments with a diameter of 20 mm were punched, added to ice-cold KRB buffer, and kept on ice.
5. After collecting all the segments needed for the incubation, the system was assembled (including to a total of 24 segments per system) and placed on ice. KRB buffer with 15 mM $NaHCO_3$ was added to the apical compartment and KRB buffer with 15 mM $NaHCO_3$ was then added to the basolateral beaker compartment. The different parts of the epithelial tissue model and a scheme of a single completed vial is presented in FIG. 1.
6. The segments were acclimatized for 30 minutes at room temperature.
7. After acclimatization, the system was placed in an incubator at 37° C. (25% air, 70% $O_2$, 5% $CO_2$) for 60 minutes.
8. Thereafter buffer from both compartments was removed, and fresh, pre-warmed KRB buffer, pH 7.4, was added to the basolateral compartment (beaker) and dose solutions containing for example various test substances were added to the apical compartment.
9. The basolateral compartment beaker was replaced by a new beaker containing fresh, pre-warmed buffer at for example 30, 60, 90 and 120 minutes.
10. Subsequently, samples were taken from the apical and basolateral compartments for further analysis either using liquid scintillation counting (LSC), UV-Absorbance, Fluorescence, High Pressure Liquid Chromatography (HPLC), Liquid chromatography-Mass Spectrometry (LCMS), Liquid chromatography-Tandem Mass Spectrometry (LC-MSMS), Enzyme-Linked Immunosorbent Assay (ELISA), or Radio-Immuno Assay (RIA).
11. After the incubation time, if needed (parts of) the epithelial tissues were collected for further analysis.

Figure 6:
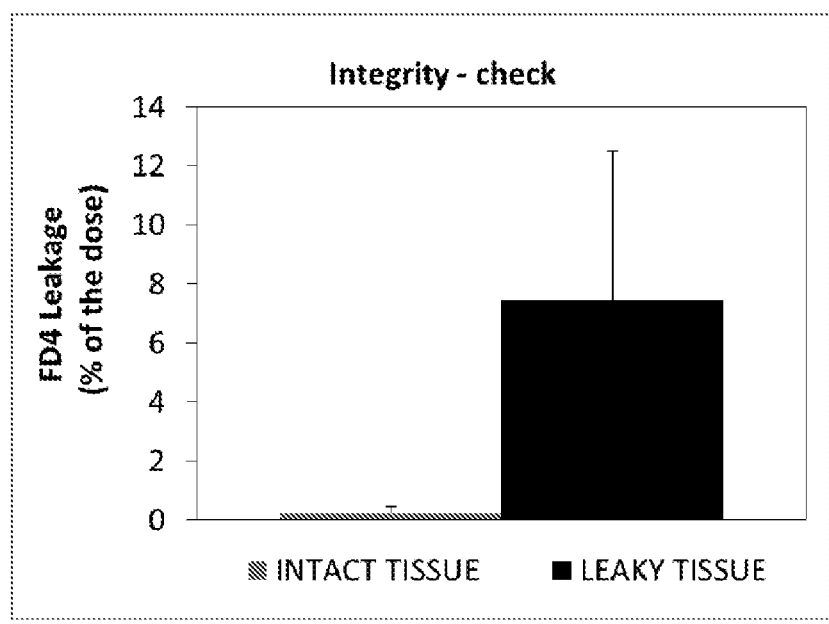
FIG. 6. Leakage of FITC conjugated dextran (FD4) as an integrity check of the tissue mounted into the epithelial tissue model. The fluorescent FD4 was added to all dose solutions and each vial indicating FD4 leakage above 0.3% was excluded from the study. FD4 data are presented as the percentage in the basolateral compartment at the end of the incubation in relation to the dose solution (% of dose solution). Data are presented as mean±standard deviation of at least three incubations.

A functional integrity marker FITC conjugated dextran (FD4; average molecular weight, 4000) was used to study the intestinal tight junction barrier function of a porcine intestinal jejunal tissue. At the start of the incubation FD4 (50 µM) was added to the apical compartment, and the leakage of FD4 across the epithelial tissue to the basolateral compartment was measured after a two hour incubation time. FD4 was determined by measuring fluorescence in the basolateral compartment as is known in the art. Leakage was expressed as % of the dose applied to the apical compartment. Leakage of FD4 of viable tissue remained below 0.3% after a two hour incubation period, whereas leakage from a non-viable, damaged or wrongly capped segments were clearly enhanced up to 7% of the dose (FIG. 6).

Example 2

Figure 7:
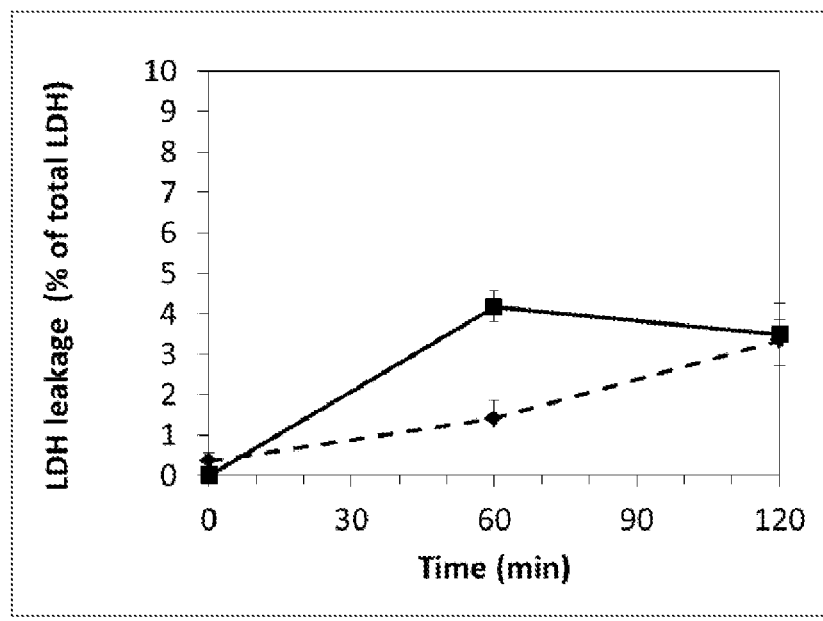
FIG. 7. Leakage of intracellular lactate dehydrogenase (LDH) to the apical and basolateral compartment during incubation time. Data are presented as the percentage of the total intracellular LDH as measured in parallel segments at the start of the experiment. LDH leakage remains below 10% during incubation time indicating no loss of viability. Data are presented as mean±standard deviation of at least three incubations.

To check the viability of tissue due to the possible presence of active proteases, the leakage of intracellular enzyme lactate dehydrogenase (LDH) to the apical and basolateral compartment during incubation time was measured. LDH is a stable cytosolic enzyme that is released upon cell damage. Leakage of LDH levels was determined as the percentage of total intracellular LDH, which were determined in parallel intestinal tissue segments at the start of the experiment. LDH activity was determined using a Roche reagent kit (Roche Diagnostics, USA) on a UV-Absorbance Spectrophotometer (FIG. 7).

Example 3

Figure 8A:
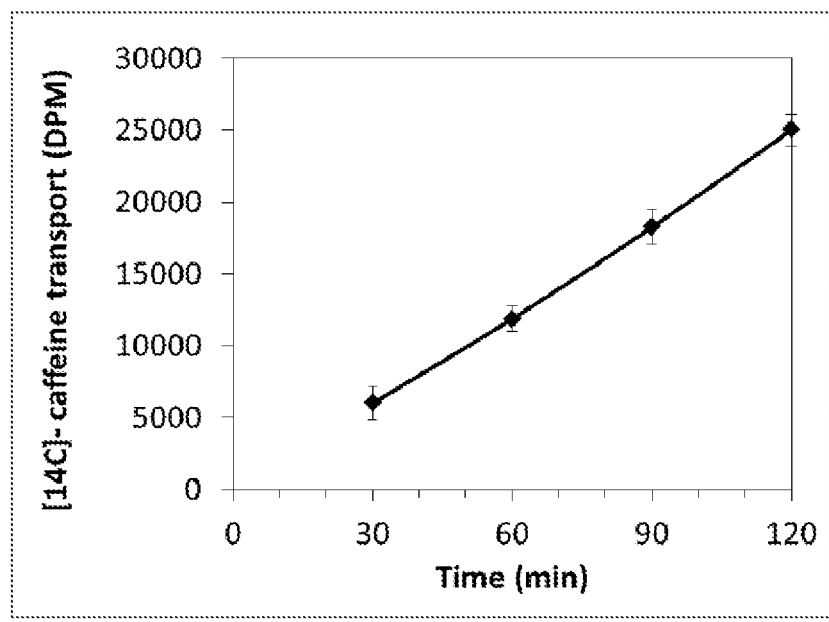
FIG. 8. The transport of [14C]-caffeine across porcine intestinal tissue in time (A) and its related calculated apparent permeability values (Papp; B). No change in Papp values indicate linear absorption of caffeine within the incubation time. Data are presented as mean±standard deviation of at least three incubations.

Transport of [14C]-caffeine across porcine jejunal tissue. Caffeine is known to be readily absorbed via passive diffusion into the epithelial cells and as such is transported via the so-called transcellular route. A clear time-dependent transport of caffeine is observed during incubation time of 120 minutes (FIG. 8A). The permeability of a compound across an epithelial barrier can be presented as the apparent permeability (Papp) value. The Papp value is defined as the initial flux of a compound across a membrane (normalized by membrane surface area and starting concentration) and is typically computed by adapting a straight line to the initial portion of the recorded amounts in the receiver compartment, disregarding the first few points when lagging of the transfer process through the membrane is evident.

The apparent permeability value (Papp) is calculated using the following equation:

$$Papp=(dQ/dt)/(A*C0),$$

where dQ/dt refers to the permeability rate (mol/s), A is the surface area filter insert (cm2) and C0 is the initial concentration (mol/L).

Figure 8B:
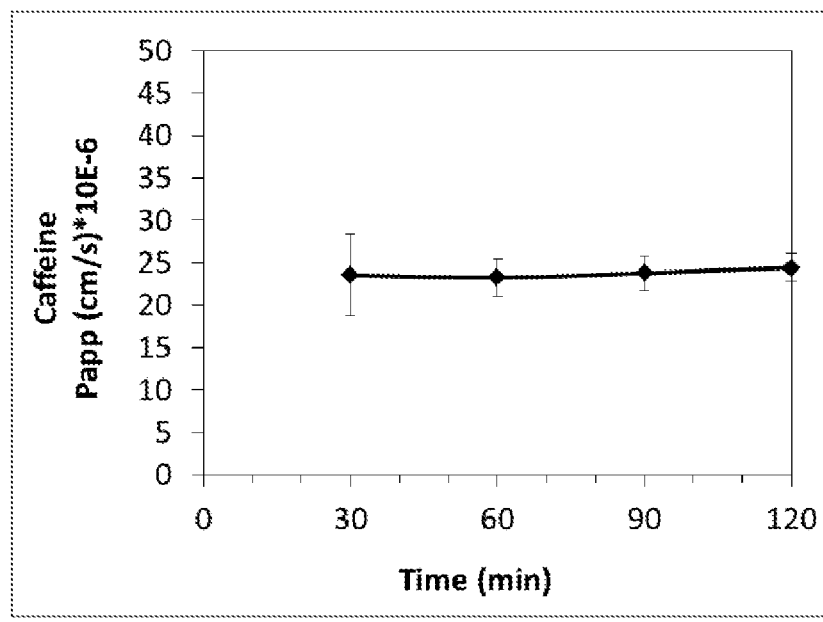

The linear transport of caffeine over time is clearly reflected in a constant Papp value over time (FIG. 8B).

Example 4

Figure 9:
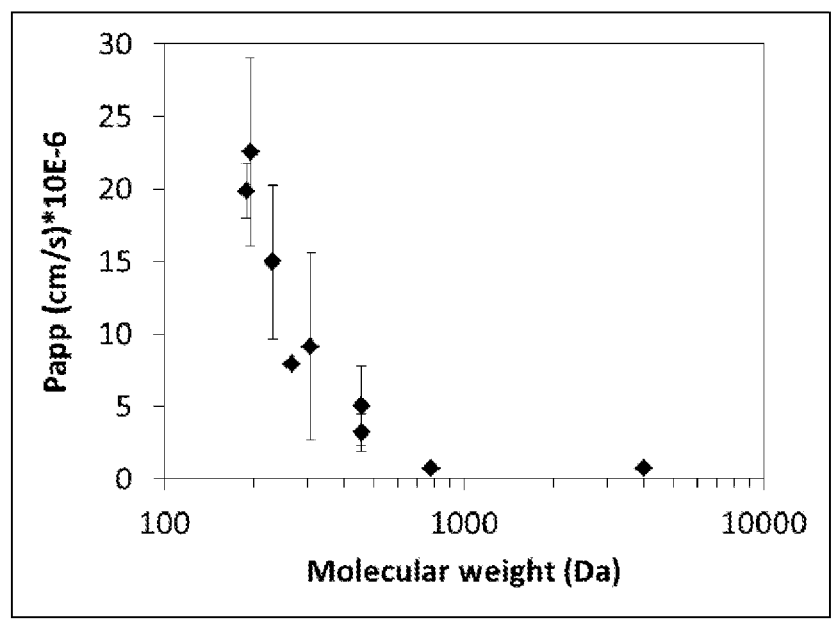
FIG. 9. The apparent permeability (Papp) values of a range of compounds as measured across porcine jejunal tissue with different molecular weights. Data are presented as mean±standard deviation of at least two incubations.

Measurement of the transport of a set of compounds with increasing molecular weights across porcine intestinal jejunal tissue from the apical to the basolateral side after dosing to the test compound (10 µM). The mean calculated Papp value of each compound is presented in FIG. 9. Each dot represents the mean Papp value of an individual compound.

Example 5

Figure 10:
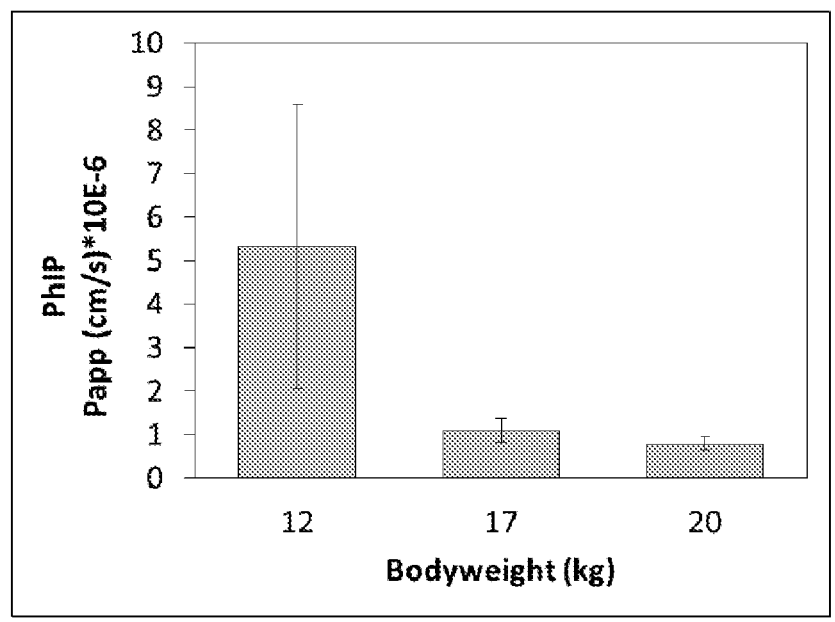
FIG. 10. The apparent permeability (Papp) values of 2-amino-1-methyl-6-phenylimidazo[4,5-b]pyridine (PhIP) across porcine jejunal tissue derived from animals with a different age. Data are presented as mean±standard deviation of at least three incubations.

Use of porcine jejunal tissue derived from animals with a different age. The transport of [14C]-PhIP (2-amino-1-methyl-6-phenylimidazo[4,5-b]pyridine), a known food mutagen, was measured across porcine jejunal tissue derived from animals with a different age. PhIP is known to have a very low permeability due to fact that it is a high affinity substrate of the breast cancer resistance protein (BCRP, gene code ABCG2), which is an efflux membrane transporter expressed at the apical side of the intestine. It is known that intestinal tissue from younger animals usually have a higher permeability of the intestinal tissue for this compound. A higher transport of [14C]-PhIP was measured across intestinal tissue derived from an animal with a body weight of 12 kg in comparison to an animal of 17 or 20 kg, which indicates a higher permeability for PhIP in younger animals (FIG. 10).

Example 6

Figure 11:
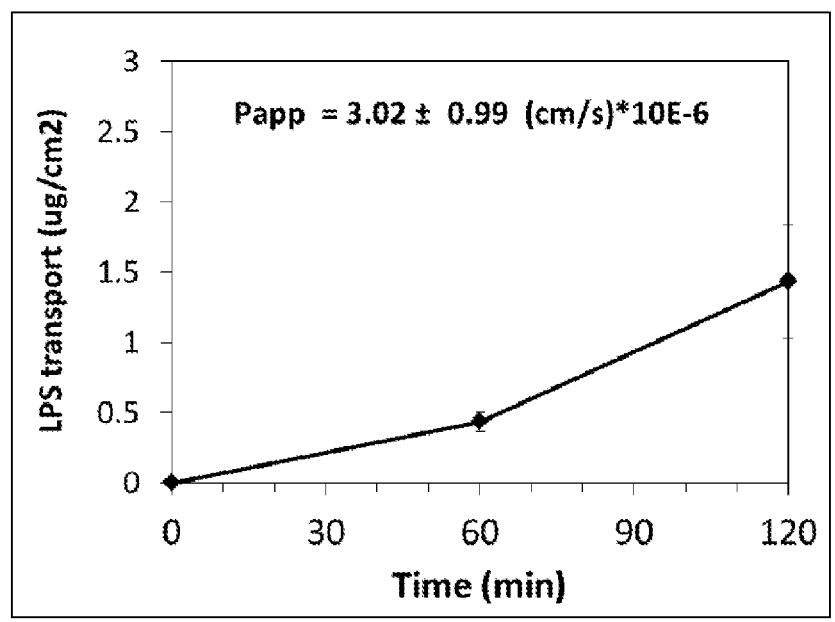
FIG. 11. The translocation of the bacterial endotoxin [14C]-lipopolysaccharide (LPS) across porcine ileal tissue in time. Data are presented as mean±standard deviation of four incubations.

Translocation of the bacterial endotoxin lipopoly-saccharide (LPS) across the porcine ileal tissue during incubation time. For ([14]-LPS a clear lag time of transport was observed between 0 and 60 minutes. The apparent permeability value of LPS was calculated over the time frame between 120 and 60 minutes (FIG. 11).

Example 7

Figure 12:
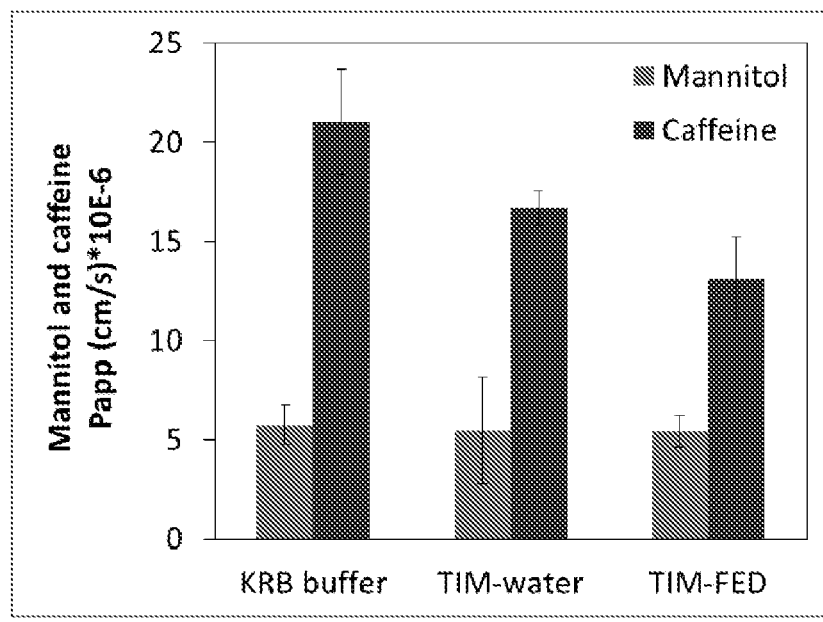
FIG. 12. The apparent permeability (Papp) values of [3H]-mannitol and [14C]-caffeine across porcine intestinal tissue after exposure to KRB buffer, on to instinal lumen samples derived from a computer controlled TNO Intestinal Model (TIM) that was fed with a glass of water (TIM-water) or with a standard FDA breakfast (TIM-fed). Data are presented as mean±standard deviation of at least three incubations.

Combination of exposure of intestinal lumen samples derived from a computer controlled TNO Intestinal Model (fed a glass of water (TIM-water) or fed a standard FDA breakfast (TIM-fed) on the transport of [3H]-mannitol and [14C]-caffeine across porcine intestinal tissue (FIG. 12).

Example 8

Figure 13:
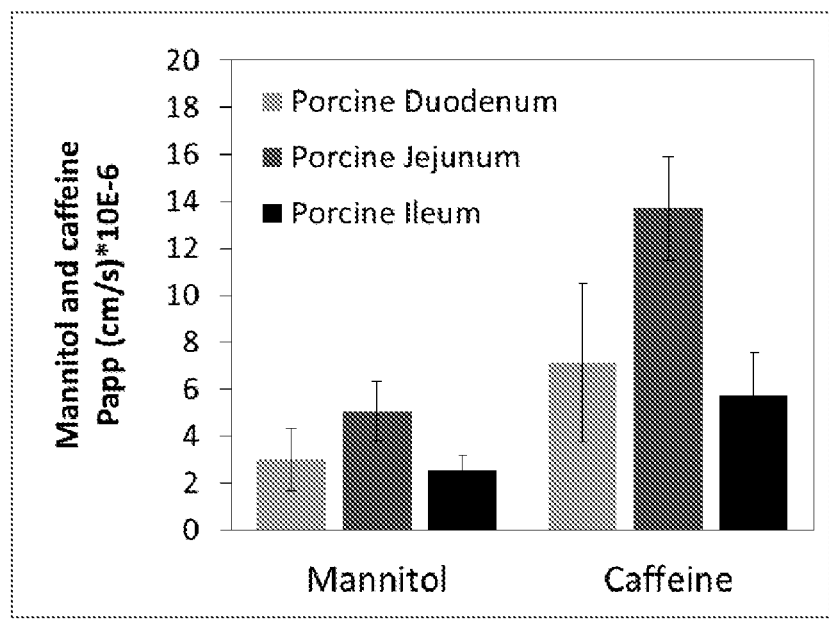
FIG. 13. The apparent permeability (Papp) values of [3H]-mannitol and [14C]-caffeine across three different segments of the porcine intestinal tract. The segments were labelled as duodenum (sample collected 10 cm after pylorus), mid jejunum (taken at approx. 5 m after pylorus), ileum (taken 1.5 m before the ileocecal junction). [3H]-mannitol is known to be a marker for the paracellular route, and [14C]-caffeine is known to be a marker for the transcellular route. Data are presented as mean±standard deviation of four incubations.

Use of different tissues derived from the same animal. In this example, the transport of [3H]-mannitol and [14C]-caffeine was measured across intestinal segments derived from three different segments from the intestine of one single pig. As indicated, caffeine is transported via the transcellular route due to its rapid passive diffusion in the epithelial cells. In contrast, the sugar mannitol is known to be transported solely via the paracellular route. Different segments of intestinal tissue were derived from one single animal. The segments were labelled as duodenum (sample collected 10 cm after pylorus), mid jejunum (taken at approx. 5 m after pylorus), ileum (taken 1.5 m before the ileocecal junction). Data are presented in FIG. 13.

Example 9

Figure 14:
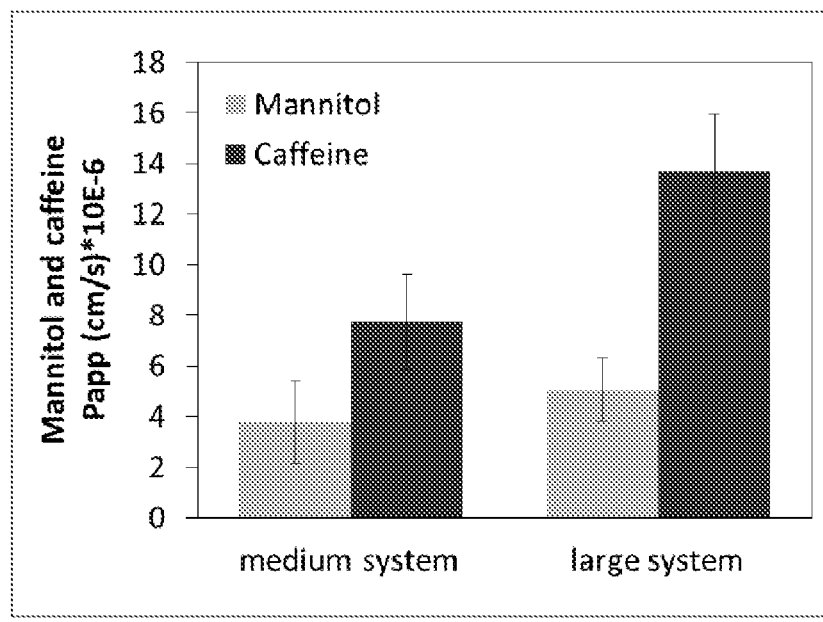
FIG. 14. The apparent permeability (Papp) values of [3H]-mannitol and [14C]-caffeine across porcine intestinal tissue mounted in a medium (2 mL crimp vial) and large system (20 mL crimp vial), respectively. Data are presented as mean±standard deviation of at least three incubations.

Use of systems with various width and volumina. The transport of [3H]-mannitol and [14C]-caffeine across porcine jejunal intestinal tissue was measured in a medium and large system, using a crimp vial of 2 and 20 mL, respectively (FIG. 14).

Example 10

Figure 15:
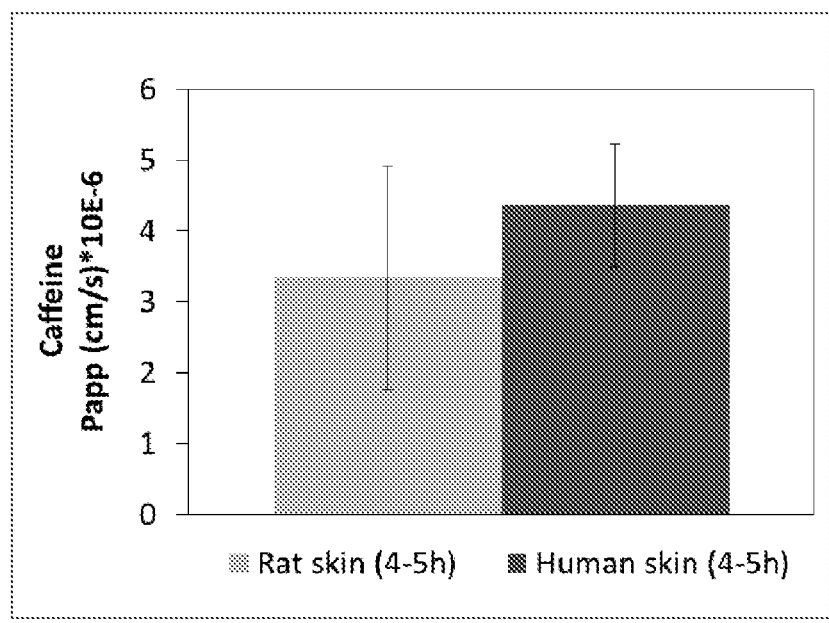
FIG. 15. The apparent permeability (Papp) values of [14C]-caffeine across abdominal skin tissue derived from two different species, rat and human. Data are presented as mean±standard deviation of at least three incubation.

Use of skin tissue derived from different species. In this example rat and human abdominal skin tissue was used. The transport of [14C]-caffeine was measured across skin tissue and the Papp values were calculated of transport between 4 and 5 hours after the start of the experiment (FIG. 15).

What is claimed is:

1. A vial for holding a segment of epithelial tissue, the vial having a neck and a first open end at a top of the neck, wherein a rim is provided at the first open end that defines a first opening, wherein an upper surface of the rim faces away from the neck,
   wherein the neck and the rim define a crimp cap receiving area for receiving a crimp cap;
   wherein the vial has a second open end located distal to the neck and wherein a ring of inert material is provided adjacent the upper surface of the rim and covers at least part of the upper surface of the rim; and
   wherein the rim extends from a perimeter of the first open end inward; said vial further comprising a receiving area for receiving a segment of epithelial tissue, wherein said receiving area is adjacent the ring of inert material, at a side of the ring of inert material facing away from the rim, wherein:
   (i) a segment of epithelial tissue is received in the receiving area, and wherein an apical side of the epithelial tissue faces the first opening and a basolateral side of the epithelial tissue faces away from the first opening; and whereby the ring of inert material is positioned on the apical side of the epithelial tissue and a crimp cap is provided on the crimp cap receiving area to provide a tight seal to the first open end of the vial; or
   (ii) a segment of epithelial tissue is received in the receiving area, and wherein a basolateral side of the epithelial tissue faces the first opening and an apical side of the epithelial tissue faces away from the first opening; and whereby the ring of inert material is positioned on the basolateral side of the epithelial tissue and a crimp cap is provided on the crimp cap receiving area to provide a tight seal to the first open end of the vial;
   wherein the vial comprises a support that is provided in the receiving area for receiving a segment of epithelial tissue, such that when the segment of epithelial tissue is received in the receiving area the basolateral or apical side of the epithelial tissue is covered by said support.
2. The vial of claim 1, wherein the support is a nylon or polypropylene mesh.
3. The vial of claim 1, wherein the ring of inert material is a Teflon ring.
4. A device for measuring absorption, transport and/or secretion across an epithelial tissue, said device comprising at least one vial according to claim 1 and at least one container for holding the at least one vial, wherein the at least one container comprises a closed bottom and an open top side facing away from the closed bottom, wherein the at least one vial is received in the at least one container with the first open end of the at least one vial facing the closed bottom of the at least one container, such that the crimp cap is located at a distance from the closed bottom such that the crimp cap does not abut the closed bottom of the at least one container.
5. The device according to claim 4, wherein the device comprises a multitude of containers holding a multitude of vials, respectively.
6. The device according to claim 5, wherein said multitude of containers comprises 6, 12, 24 or 48 containers, wherein the device has a footprint (length x width) of 127.76×85.48 mm.
7. A method for generating a vial with a segment of epithelial tissue, comprising:
   providing the vial according to claim 1,
   preparing the segment of an epithelial tissue,
   mounting the support onto the basolateral side of the epithelial segment,
   mounting the ring of inert material onto the apical side of the epithelial tissue,
   mounting the supported segment on the upper surface of the rim, such that the ring of inert material abuts the upper surface and the apical side of the epithelial tissue faces the first opening of the vial, and
   providing the crimp cap on the cap receiving area to obtain a tight seal on the first open end of the vial.
8. A method for generating a multitude of vials with a segment of epithelial tissue, comprising:
   (a) performing the method of claim 7 to prepare a first vial,
   (b) cooling at least the first open end comprising the segment of an epithelial tissue, repeating steps (a) and (b) until the multitude of vials is prepared.
9. A method for measuring absorption, transport and/or secretion across an epithelial tissue, the method comprising
   providing the device according to claim 4, wherein an epithelial tissue is provided in the at least one vial of the device,
   providing a buffered medium in the at least one vial onto the apical site of the segment of epithelial tissue,
   providing a buffered medium to the at least one container, wherein a height of the buffered medium in the at least one vial is equal to a height of the buffered medium in the at least one container,
   applying a substance to the medium at the apical site of the segment of epithelial tissue, and
   measuring the amount of substance that accumulates in the medium of the at least one container.
10. The method of claim 9, wherein the substance is labeled.
11. The method of claim 9, further comprising adding a marker to the apical site of the segment of epithelial tissue, and measuring the amount of marker that that appears in the medium of the at least one container.
12. A method for measuring absorption, transport and/or secretion across an epithelial tissue, the method comprising
   providing the device according to claim 5 comprising an epithelial tissue,
   providing a relevant buffered medium in the vials onto the apical site of the segment of epithelial tissue in the vials,
   providing a relevant buffered medium to the containers, wherein a height of the buffered medium in the vials is equal to a height of the buffered medium in the containers, applying a substance to the medium at the apical site of the segment of epithelial tissue in the vials, and measuring the amount of substance that accumulates in the medium of the containers.

13. A vial for holding a segment of epithelial tissue, the vial having a neck and a first open end at a top of the neck, wherein a rim is provided at the first open end that defines a first opening, wherein an upper surface of the rim faces away from the neck,
 wherein the neck and the rim define a crimp cap receiving area for receiving a crimp cap;
 wherein the vial has a second open end located distal to the neck and wherein a support is provided adjacent the upper surface of the rim and covers at least part of the upper surface of the rim; and
 wherein the rim extends from a perimeter of the first open end inward; said vial further comprising a receiving area for receiving a segment of epithelial tissue, wherein said receiving area is adjacent the support, at a side of the support facing away from the rim; wherein:

(i) a segment of epithelial tissue is received in the receiving area, and wherein an apical side of the epithelial tissue faces the first opening and is covered by said support, and a basolateral side of the epithelial tissue faces away from the first opening, or (ii) a segment of epithelial tissue is received in the receiving area, and wherein a basolateral side of the epithelial tissue is covered by said support and faces the first opening, and an apical side of the epithelial tissue faces away from the first opening;

wherein said vial comprises a ring of inert material; and wherein, when a segment of epithelial tissue is received in the receiving area, the ring of inert material is positioned on the apical or basolateral side of the epithelial tissue not covered by said support, and the crimp cap is provided on the crimp cap receiving area to provide a tight seal to the first open end of the vial.

* * * * *